United States Patent [19]
Koszyk et al.

[11] Patent Number: 4,937,357
[45] Date of Patent: Jun. 26, 1990

[54] INTERMEDIATES FOR ANTIVIRAL COMPOUNDS

[75] Inventors: Francis J. Koszyk, Chicago; Richard A. Partis, Evanston; Richard A. Mueller, Glencoe, all of Ill.

[73] Assignee: G. D. Searle & Co., Skokie, Ill.

[21] Appl. No.: 410,638

[22] Filed: Sep. 26, 1989

Related U.S. Application Data

[63] Continuation-in-part of Ser. No. 266,718, Nov. 3, 1988, Pat. No. 4,876,268.

[51] Int. Cl.$^5$ ............................................ C07D 207/12
[52] U.S. Cl. .................................................... 548/556
[58] Field of Search ............................................ 548/556

[56] References Cited

U.S. PATENT DOCUMENTS 3,312,716 4/1967 Biel et al. .......................... 260/326.5
4,182,767 1/1980 Murai et al. .......................... 424/267
4,639,436 1/1987 Junge et al. ............................ 514/24
4,849,430 7/1989 Fleet et al. ............................ 514/315

FOREIGN PATENT DOCUMENTS 8703903 7/1987 PCT Int'l Appl. .

OTHER PUBLICATIONS

Frank, Antimicrob. Agents Chemother. 31, 1369–1374 (1987).
Sunkara et al., Soc. Complex Carbohyd., 17th Ann. Meet., San Antonio, Nov. 3–5, 1988, Abstract 9.

Primary Examiner—David B. Springer
Attorney, Agent, or Firm—Scott J. Meyer; James W. Williams, Jr.

[57] ABSTRACT

N-alkyl, N-hydroxylalkyl and N-alkanoyl derivatives of 1,4-dideoxy-1,4-imino-L-arabinitol are disclosed in which the alkyl group has from 4 to about 9 carbon atoms, the hydroxyalkyl group has from 2 to about 5 carbon atoms and the alkanoyl group has from 3 to about 12 carbon atoms. These compounds are useful intermediates for the preparation of acylated derivatives thereof which have antiviral activity.

11 Claims, No Drawings

INTERMEDIATES FOR ANTIVIRAL COMPOUNDS

CROSS-REFERENCE TO RELATED APPLICATION

This is a continuation-in-part of copending application Ser. No. 07/266,718, filed Nov. 3, 1988, U.S. Pat. No. 4,876,268, issued Oct. 24, 1989.

BACKGROUND OF THE INVENTION

This invention relates to novel intermediates for the preparation of antiviral compounds and, more particularly, to N-alkyl, N-hydroxyalkyl and N-alkanoyl derivatives of 1,4-dideoxy-1,4-imino-L-arabinitol. These intermediates are particularly useful for the preparation of acylated derivatives thereof which are inhibitors of visna virus, a pathogenic virus for sheep and goats. These antiviral compounds also have potential use for the treatment of acquired immune deficiency syndrome (AIDS) and AIDS-related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or CD4+ cells). See, e.g., Gallo et al., *Science* 224, 500–503 (1984), and Popovic et al., Ibid., 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [*Ann. Virol. Inst. Pasteur* 135 E, 119–134 (1984)], while HIV-2 was more recently isolated by Montagnier and his coworkers in 1986 [*Nature* 326, 662–669 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, *Science* 241, 426–432 (1988).

The first drug to be approved by the U.S. Food and Drug Administration (FDA) for treatment of AIDS was zidovudine, better known under its former name azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

The HIV inhibitory activity of 1,4-dideoxy-1,4-imino-L-arabinitol and its N-methyl derivative is disclosed in copending application Ser. No. 07/249,144, filed Sept. 26, 1988.

BRIEF DESCRIPTION OF THE INVENTION

In accordance with the present invention, novel N-alkyl, N-hydroxyalkyl and N-alkanoyl derivatives of 1,4-dideoxy-1,4-imino-L-arabinitol are provided in which the alkyl group has from 4 to about 9 carbon atoms, the hydroxyalkyl group has from 2 to about 5 carbon atoms and the alkanoyl group has from 3 to about 12 carbon atoms.

1,4-dideoxy-1,4-imino-L-arabinitol is a five-membered heterocyclic compound having nitrogen in the ring and 3 hydroxyl groups. It is thus described by a systematic chemical name as a sugar derivative in which the five-membered ring is considered as a mimic of furanose, with nitrogen instead of oxygen in the ring. It can also be described structurally as a derivative of pyrrolidine. It can be prepared by joining the C-1 and C-4 of xylose together with nitrogen to form the pyrrolidine ring as described by Fleet and Smith, *Tetrahedron* 42, 5685–5692 (1986), or from xylitol in which only hydroxyl groups from C-1 and C-4 of xylose are left unprotected as disclosed by Fleet et al, *Tetrahedron Lett.* 26, 3127–3130 (1985).

The structure of the novel N-alkyl, N-hydroxyalkyl and N-alkanoyl derivatives of 1,4-dideoxy-1,4-imino-L-arabinitol can be represented as follows:

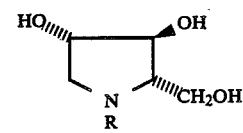

wherein R=$C_4$–$C_9$ alkyl, $C_2$–$C_5$ hydroxyalkyl, or $C_3$–$C_{12}$ alkanoyl.

These novel compounds are useful intermediates for the preparation of acylated derivatives thereof which have antiviral activity. In the acylated derivatives, all the free hydroxyl groups are acylated with acyl groups having from one to six carbon atoms.

Illustrative examples of the novel N-alkyl, N-hydroxyalkyl and N-alkanoyl derivatives of 1,4-dideoxy-1,4-imino-L-arabinitol are the following compounds:

1,4-(Butylimino)-1,4-dideoxy-L-arabinitol,
1,4-(Pentylimino)-1,4-dideoxy-L-arabinitol,
1,4-(Hexylimino)-1,4-dideoxy-L-arabinitol,
1,4-(Heptylimino)-1,4-dideoxy-L-arabinitol,
1,4-(2-Ethylbutylmino)-1,4-dideoxy-L-arabinitol,
1,4-(Octylimino)-1,4-dideoxy-L-arabinitol,
1,4-(Nonylimino)-1,4-dideoxy-L-arabinitol,
1,4-([2-Hydroxyethyl]imino)-1,4-dideoxy-L-arabinitol,
1,4-([3-Hydroxypropyl]imino)-1,4-dideoxy-L-arabinitol,
1,4-([4-Hydroxybutyl]imino)-1,4-dideoxy-L-arabinitol,
1,4-([5-Hydroxypentyl]imino)-1,4-dideoxy-L-arabinitol,
1,4-([2-Acetyloxyethyl]imino)-1,4-dideoxy-L-arabinitol,
1,4-([5-Acetyloxypentyl]imino)-1,4-dideoxy-L-arabinitol,
1,4-(Propionylimino)-1,4-dideoxy-L-arabinitol,
1,4-(2-Methylpropionylimino)-1,4-dideoxy-L-arabinitol.

Illustrative examples of antiviral compounds which can be made by acylation of the foregoing intermediates are the following compounds:

1,4-(Butylimino)-1,4-dideoxy-L-arabinitol, triacetate,
1,4-(Hexylimino)-1,4-dideoxy-L-arabinitol, triacetate,
1,4-(Nonylimino)-1,4-dideoxy-L-arabinitol, triacetate,
1,4-(Butylimino)-1,4-dideoxy-L-arabinitol, tributyrate,
1,4-(Butylimino)-1,4-dideoxy-L-arabinitol, tripropionate,
1,4-([5-Hydroxypentyl]imino)-1,4-dideoxy-L-arabinitol, triacetate,
1,4-([2-Acetyloxyethyl]imino)-1,4-dideoxy-L-arabinitol, triacetate,
1,4-([2-Acetyloxyethyl]imino)-1,4-dideoxy-L-arabinitol, tributyrate,
1,4-(5-Acetyloxypentyl]imino)-1,4-dideoxy-L-arabinitol, triacetate,
1,4-([5-Acetyloxypentyl]imino)-1,4-dideoxy-L-arabinitol, tributyrate,
1,4-(Propionylimino)-1,4-dideoxy-L-arabinitol, triacetate, and
1,4-(2-Methylpropionylimino)-1,4-dideoxy-L-arabinitol, triacetate.

Preferred method of preparation of the N-alkyl, N-hydroxyalkyl and N-alkanoyl substituted amine compounds is via catalytic reductive amination of the corresponding aldehyde or hydroxyaldehyde equivalent or by hydrogen transfer reductive alkylation. The hydroxyaldehyde equivalent may exist in a hemiacetal structure. Hydroxyaldehydes or their equivalents can be used where the hydroxyl group is protected, followed by removal of the protecting group. Hydride reduction is a preferred method of reductive alkylation where catalytic conditions would cause destruction of the starting material or products or overreaction. Cyanoborohydride reagents are most convenient hydride donors when acid stability is beneficial, e.g., when a rapid equilibrium between various chemical intermediates is desired. Examples of such equilibria can be hydroxyalkylaldehyde to hemiacetal, aminoacetal to amine and aldehyde and aminoacetal to an amine containing a double bond.

Illustratively, the N-alkyl derivatives can be prepared by hydrogenation of the starting amine together with an appropriate aldehyde in suitable solvent medium in the presence of palladium black catalyst as described, e.g., by Fleet et al in copending application Ser. No. 249,144, filed Sept. 26, 1988. In an alternative method, the amine is reductively aminated with sodium cyanoborohydride in the presence of a molecular sieve instead of reduction with the palladium black hydrogenation catalyst.

Although specific methods of production are described herein, it will be appreciated that the novel intermediates claimed herein are not limited to any particular method of production.

The foregoing acylated compounds can be demonstrated to have inhibitory activity against visna virus in a conventional plaque reduction assay. Visna virus, a lentivirus genetically very similar to the AIDS virus, is pathogenic for sheep and goats. See Sonigo et al., *Cell* 42, 369–382 (1985); Haase, *Nature* 322, 130–136 (1986). Inhibition of visna virus replication in vitro also is a useful model for human immunodeficiency virus (HIV), and its inhibition by test compounds has been described by Frank et al., *Antimicrobial Agents and Chemotherapy* 31 (9), 1369–1374 (1987).

The N-butyl derivative of 1,5-dideoxy-1,5-imino-D-glucitol, also referred to as N-butyl-deoxynojirimycin (N-Bu-DNJ), was used as a control standard herein for comparison with the acylated derivatives of the novel compounds of this invention. The HIV inhibitory activity of N-Bu-DNJ is described in U.S. Pat. No. 4,849,430.

Inhibitory activity can also be demonstrated by the acylated derivatives against alpha- and beta-glucosidase enzymes. In some cases, the intermediates also have effective inhibitory activity against visna virus, cytomegalovirus (CMV) and/or the alpha- and beta-glucosidases.

DETAILED DESCRIPTION OF THE INVENTION

The following detailed examples will further illustrate the invention although it will be understood that the invention is not limited to these specific examples.

EXAMPLE 1

A. 1,4-Dideoxy-1,4-imino-L-arabinitol hydrochloride

B. 1,4-Dideoxy-1,4-imino-L-arabinitol

The title compounds were prepared by the method described by Fleet and Smith, Tetrahedron 42, 5685–5692 (1986), to prepare the D-isomers, except that L-xylose was used as the starting material instead of D-xylose

EXAMPLE 2

1,4-Dideoxy-1,4-([2-hydroxyethyl]imino)-L-arabinitol

To a solution of the title product of Example 1A (1.44 g, 8.50 mmoles) in 25 ml of methanol was added a solution of sodium bicarbonate (714 mg, 8.50 mmoles) in 10 ml of water. After stirring for a few minutes, the solvent was removed on a rotary evaporator. The residue was then dissolved in anhydrous ethanol, and the solvent was removed on a rotary evaporator. The residue was dissolved in a mixture of 29 ml of methanol and 1.5 ml of acetic acid. To the resulting solution was added glycolaldehyde dimer (1.02 g, 8.50 mmoles), 5 g of 4 Å molecular sieves, and then, in portions, sodium cyanoborohydride (553 mg, 8.81 mmoles). After stirring overnight at room temperature, the mixture was filtered, and the solvent was removed on a rotary evaporator. Chromatography of the residue on silica gel using 50–50 ethyl acetate-methanol as eluant gave the title compound (1.82 g) as an oil. The compound was identified by proton and carbon NMR spectrometry.

EXAMPLE 3

1,4-([2-Acetyloxyethyl]imino)-1,4-dideoxy-L-arabinitol, triacetate

To a solution of the title product of Example 2 (343 mg, 1.9 mmoles) in 10 ml of pyridine was added 4 ml of acetic anhydride. The residue was stirred for one hour at room temperature, and then at reflux for 5 minutes. After cooling, the mixture was poured into 30 ml of ice water and extracted with three portions of ethyl acetate. The combined organic extracts were washed with 25 ml of dilute hydrochloric acid, dried over sodium sulfate, filtered, and the solvent removed on a rotary evaporator. Chromatography of the residue on silica gel using a gradient of 50 to 75% ethyl acetate-hexane as eluant gave the title compound (418 mg) as an oil.

Analysis for $C_{15}H_{23}NO_8$ (MW 345.35): Calcd.: C, 52.17; H, 6.71; N, 4.06. Found: C, 51.77; H, 6.66; N, 4.00.

EXAMPLE 4

1,4-(Butylimino)-1,4-dideoxy-L-arabinitol

The title compound (822 mg) was prepared as an oil by the method of Example 2 by using N-butyraldehyde (1.27 g) instead of glycolaldehyde dimer, and by using 1.50 g of the product of Example 1A as the starting material. The title compound was identified by proton and carbon NMR spectrometry.

EXAMPLE 5

1,4-(Butylimino)-1,4-dideoxy-L-arabinitol, triacetate

The title compound (418 mg) was prepared as an oil by the method of Example 3, using the product of Example 4 instead of the product of Example 2 as the starting material, and using 35% ethyl acetatehexane as the chromatography eluant.

Analysis for $C_{15}H_{25}NO_6$ (MW 315.37): Calcd.: C, 57.13; H, 7.99; N, 4.44. Found: C, 56.84; H, 7.85; N, 4.42.

EXAMPLE 6

1,4-(Hexylimino)-1,4-dideoxy-L-arabinitol

To a solution of the title product of Example 1B (250 mg, 1.88 mmoles) in a mixture of 6.3 ml of methanol and 0.3 ml of acetic acid was added 1.1 g of 4 Å molecular sieves, n-hexanal (377 mg, 3.76 mmoles) and then, in portions, sodium cyanoborohydride (123 mg, 1.96 mmoles). After stirring overnight at room temperature, the mixture was filtered, and the solvent was removed on a rotary evaporator. Chromatography of the residue on silica gel using 15% methanol—2.5% ammonium hydroxide—82.5% ethyl acetate as eluant gave a partially purified product. The material was dissolved in 5 ml of 50-50 trifluoroacetic acid-water. After 15 minutes the solvent was removed on a rotary evaporator. The residue was dissolved in water, passed through a basic ion exchange resin, and eluted with water. Appropriate fractions were then passed through an acidic ion exchange resin and eluted with aqueous ammonium hydroxide. Appropriate fractions were lyophilized to give the title compound (123 mg) as an oil.

Analysis for $C_{11}H_{23}NO_3$ (MW 217.31): Calcd.: C, 60.79; H, 10.67; N, 6.45. Found: C, 60.36; H, 10.50; N, 6.35.

EXAMPLE 7

1,4-(Hexylimino)-1,4-dideoxy-L-arabinitol, triacetate

The title compound (56 mg) was prepared as an oil by the method of Example 3, using the product of Example 6 (64 mg) as the starting material, and using 25% ethyl acetate-hexane as the chromatography eluant.

Analysis for $C_{17}H_{29}NO_6$ (MW 343.42): Calcd.: C, 59.46; H, 8.51; N, 4.08. Found: C, 59.13; H, 8.50; N, 4.04.

EXAMPLE 8

1,4-([4-Chlorophenyl]methylimino)-1,4-dideoxy-L-arabinitol

To a solution of the title product of Example 1B (447 mg, 3.36 mmole) in a mixture of 11 ml of methanol and 0.5 ml of acetic acid was added 2.0 g of 4 Å molecular sieves, 948 mg (6.72 mmoles) of 4-chlorobenzaldehyde, and then, in portions, 220 mg (3.49 mmoles) of sodium cyanoborohydride. After stirring overnight at room temperature the mixture was filtered, and the solvent removed on a rotary evaporator. Chromatography of the residue over silica gel using 10% methanol—2.5% ammonium hydroxide—87.5% ethyl acetate as eluant followed by crystallization from ethyl acetate-hexane gave the title compound (189 mg) as a white solid, m.p. 94° C.

Analysis for $C_{12}H_{16}ClNO_3$ (MW 257.72): Calcd.: C, 55.92; H, 6.25; N, 5.44. Found: C, 55.54; H, 6.21; N, 5.44.

EXAMPLE 9

1,4-([4-Ethylphenyl]methylimino)-1,4-dideoxy-L-arabinitol

The title compound (190 mg) was prepared as a waxy solid by the method of Example 6 by using 4-ethylbenzaldehyde (785 mg) instead of hexanal, using 390 mg of the product of Example 1B, and by using 25% methanol—2.5% ammonium hydroxide—72.5% ethyl acetate as the chromatography eluant.

Analysis for $C_{14}H_{21}NO_3 \cdot \frac{1}{2}H_2O$ (MW 253.55): Calcd.: C, 66.32; H, 8.45; N, 5.52. Found: C, 66.29; H, 8.29; N, 5.46.

EXAMPLE 10

1,4-(0 4-Ethylphenyl]methylimino)-1,4-dideoxy-L-arabinitol, triacetate

The title compound (132 mg) was prepared as an oil by the method of Example 3, using the product of Example 9 (87 mg) instead of the product of Example 2 as the starting material, and using 50-50 ethyl acetate-hexane as the chromatography eluant.

Analysis for $C_{20}H_{27}NO_6$ (MW 377.44): Calcd.: C, 63.65; H, 7.21; N, 3.71. Found: C, 63.59; H, 7.37; N, 3.61.

EXAMPLE 11

1,4-(Nonylimino)-1,4-dideoxy-L-arabinitol

The title compound was prepared by the method of Example 2 using nonanal (557 mg) instead of glycolaldehyde dimer, 333 mg of the product of Example 1A, and 15% methanol—2.5% ammonium hydroxide—82.5% ethyl acetate as the chromatography eluant. The product, characterized by spectral methods, was used below without further purification.

EXAMPLE 12

1,4-(Nonylimino)-1,4-dideoxy-L-arabinitol, triacetate

The title compound was prepared by the method of Example 3, using the product of Example 11 instead of the product of Example 2 as the starting material, and using a gradient of 20 to 30% ethyl acetate-hexane as the chromatography eluant.

Analysis for $C_{20}H_{35}NO_6$ (MW 385.51): Calcd.: C, 62.31; H, 9.15,; N, 3.63. Found: C, 62.42; H, 8.80; N, 3.51.

EXAMPLE 13

2-Hydroxytetrahydropyran

Dihydropyran (23 g, 274 mmoles) was added to 100 ml of 0.2 molar aqueous hydrochloric acid and the resulting mixture was stirred at room temperature. The mixture was then neutralized with dilute aqueous sodium hydroxide solution. Distillation at reduced pressure through a Vigreaux column gave the title compound as a water-white liquid. $^1H$ and $^{13}C$ NMR spectra confirmed the structure of the compound.

EXAMPLE 14

1,4-([5-Hydroxypentyl]imino)-1,4-dideoxy-L-arabinitol

The title compound (360 mg) was prepared by the method of Example 6 by using the product of Example 13 (897 mg) instead of n-hexanal, and by using 390 mg of the product of Example 1B.

Analysis for $C_{10}H_{21}NO_4 \cdot \frac{1}{4}H_2O$ (MW 223.80): Calcd.: C, 53.66; H, 9.68; N, 6.28. Found: C, 53.60; H, 9.82; N, 6.23.

EXAMPLE 15

1,4-([5-Acetyloxypentyl]imino)-1,4-dideoxy-L-arabinitol, triacetate

The title compound was prepared as an oil by the method of Example 3 by using the product of Example 14 instead of the product of Example 2.

Analysis for $C_{18}H_{29}NO_8$ (MW 387.43): Calcd.: C, 55.81; H, 7.55; N, 3.62. Found: C, 55.75; H, 7.47; N, 3.51.

EXAMPLE 16

1,4-([3-Propylphenyl]imino)-1,4-dideoxy-L-arabinitol

A solution of the title product of Example 1B (250 mg, 1.88 mmoles) and hydrocinnamaldehyde (504 mg, 3.76 mmoles) in methanol was hydrogenated in the presence of 5% palladium and carbon at room temperature under a pressure of 5 pounds per square inch of hydrogen for 70 hours. The catalyst was filtered off and the solvent removed on a rotary evaporator. Chromatography of the residue on silica gel using 20% methanol—2.5% ammonium hydroxide—77.5% ethyl acetate as eluant followed by crystallization from toluene gave the title compound as a light tan crystalline solid (153 mg), m.p. 63° C.

Analysis for $C_{14}H_{21}NO_3 \cdot \frac{1}{4}H_2O$ (MW 255.83): Calcd.: C, 65.75; H, 8.47; N, 5.48. Found: C, 65.64; H, 8.43; N, 5.52.

EXAMPLE 17

1,4-(Benzyloxycarbonylimino)-1,4-dideoxy-L-arabinitol

A. Methyl 2-azido-2-deoxy-5-0-p-toluenesulfonyl-α-L-lyxofuranoside was prepared by the method described by Fleet and Smith, Tetrahedron 42, 5685–5692 (1986), for the preparation of the corresponding D-isomer except that L-xylose was used herein as the starting material instead of D-xylose.

B. Methyl 2,5-dideoxy-2,5-imino-α-L-lyxofuranoside, tosylate salt, was prepared from the azido tosylate product of Part A, above, by hydrogenation of a solution of 83 grams of said azido tosylate in ethanol in the presence of 5% palladium on carbon under a pressure of 5 pounds per square inch of hydrogen for 4½ hours. The catalyst was filtered off and the solvent removed on a roatry evaporator. Crystallization of the residue from methylene chloride-methanol-ethyl acetate gave methyl 2,5-dideoxy-2,5-imino-a-L-lyxofuranoside, tosylate salt, as a pure white crystalline solid, m.p. 115°–116°. The structure of this novel compound was confirmed by spectroscopic methods.

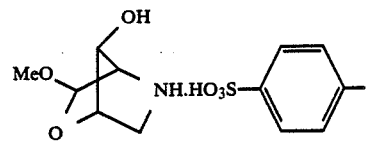

C. The title compound, 1,4-(Benzyloxycarbonylimino)-1,4-dideoxy-L-arabinitol, was prepared from the tosylate salt of Part B, above, as follows. To a mixture of 25.0 grams of said tosylate salt, 250 ml of ethyl acetate, and 125 ml of saturated aqueous sodium bicarbonate at 0° was added dropwise benzyl chloroformate (17.5 g) with rapid stirring. After 1.0 hour, the layers were separated, and the aqueous layer was extracted with ethyl acetate. The combined organic layers were dried over sodium sulfate, the drying agent was removed by filtration, and the filtrate was removed on a rotary evaporator. The pale yellow residue was then dissolved in a 4:1 mixture of trifluoroacetic acid and water (220 ml). After 0.5 hour at room temperature, the solvents were removed on a rotary evaporator and the residue was dried by azeotropic distillation with benzene. The residue was then dissolved in ethanol (225 ml), and a solution of sodium borohydride (2.24 g) in water (23 ml) was added dropwise. After stirring for 15 minutes at room temperature, ammonium chloride (2.25 g) was added, and the solvent removed on a rotary evaporator. The residue was partitioned between ethyl acetate and water, and the aqueous layer was extracted with four portions of ethyl acetate. The combined organic extracts were dried over sodium sulfate, the drying agent was removed by filtration and the solvent was removed on a rotary evaporator. Chromatography of the residue on silica gel using a gradient of 0–10% methanol-ethyl acetate gave the title compound, 1,4-(Benzyloxycarbonylimino)-1,4-dideoxy-L-arabinitol, (15.2 g) as a pale tan solid, m.p. 125°–126.5°. The structure was confirmed by spectroscopic methods.

EXAMPLE 18

1,4-(Methylimino)-1,4-dideoxy-L-arabinitol

A mixture of the title product of Example 17, Part C (500 mg), 100 mg of 10% palladium on carbon, 17 ml of ethanol, and 2 ml of cyclohexene was stirred at reflux under a nitrogen atmosphere for 2.5 hours. After cooling, 430 μl of a 37% aqueous solution of formaldehyde was added and the resulting solution stirred overnight at room temperature. A further portion (50 mg) of 10% palladium on carbon and 1 ml of cyclohexene were added and stirring was continued at reflux for 6 hours. The solids were removed by filtration and the solvent removed on a rotary evaporator. Chromatography on silica gel using 40% methanol—2.5% ammonium hydroxide—57.5% ethyl acetate as eluant gave a partially purified product. The residue was passed through an acidic ion exchange resin and eluted with dilute aqueous ammonium hydroxide. The appropriate fractions were lyophilized to give the title compound as a very pale yellow oil (160 mg).

Analysis for $C_6H_{13}NO_3 \cdot \frac{3}{8}H_2O$ (MW 153.94): Calcd.: C, 46.83; H, 9.01; N, 9.10. Found: C, 46.86; H, 9.08; N, 9.61.

EXAMPLE 19

1,4-(Methylimino)-1,4-dideoxy-L-arabinitol, triacetate

The title compound was prepared by the method of Example 3 using the product of Example 18 instead of the title product of Example 2. The compound was identified by $^1$H NMR spectroscopy.

EXAMPLE 20

1,4-(Benzyloxycarbonylimino)-1,4-dideoxy-L-arabinitol, triacetate

To a solution of the title product of Example 17, Part C (1.00g) in 25 ml of pyridine was added 5 ml of acetic anhydride. After standing overnight at room temperature, the mixture was partitioned between ethyl acetate and water. The organic layer was washed successively with two portions of aqueous copper sulfate solution, water, and brine. After drying over anhydrous sodium sulfate, the solution was filtered, and the solvent was removed on a rotary evaporator. Chromatography of the residue on silica gel using 35% ethyl acetate-hexane as eluant gave the title compound as an oil.

Analysis for $C_{19}H_{23}NO_8$ (MW 393.40): Cald.: C, 58.01; H, 5.89; N, 3.56. Found: C, 57.76; H, 5.78; N, 3.51.

EXAMPLE 21

1,4-Imino-1,4-dideoxy-L-arabinitol, triacetate

To a solution of the title product of Example 20 (3.00g) in a mixture of 72 ml of ethanol and 8 ml of cyclohexene was added 300 mg of 10% palladium on carbon. The resulting mixture was stirred at reflux for 5 hours under nitrogen and then cooled. The catalyst was removed by filtration and the solvent was removed on a rotary evaporator. Chromatography of the residue on silica gel using a gradient of 0% to 10% methanol—ethyl acetate gave the title compound as an oil. The structure was verified by $^1$H NMR spectrometry.

EXAMPLE 22

1,4-(Benzyloxycarbonylimino)-1,4-dideoxy-L-arabinitol, tributyrate

The title compound was prepared by the method of Example 20 by using butyric anhydride instead of acetic anhydride, and by conducting the reaction at reflux for 0.5 hour instead of at room temperature.

Analysis for $C_{25}H_{35}NO_8$ (MW 477.56): Calcd.: C, 62.88; H, 7.39; N, 2.93. Found: C, 62.70; H, 7.44; N, 2.88.

EXAMPLE 23

1,4-Imino-1,4-dideoxy-L-arabinitol, tributyrate

The title compound was prepared by the method of Example 21 by using the product of Example 22 instead of the product of Example 20.

Analysis for $C_{17}H_{29}NO_6$ (MW 343.42): Calcd.: C, 59.46; H, 8.51; N, 4.08. Found: C, 59.06; H, 8.30; N, 4.02.

EXAMPLE 24

1,4-(Benzyloxycarbonylimino)-1,4-dideoxy-L-arabinitol, triisobutyrate

The title compound was prepared by the method of Example 22 by using isobutyric anhydride instead of acetic anhydride, by the addition of 4-dimethylaminopyridine in catalytic amount, and by using a gradient of 25% to 50% ethyl acetate-hexane as the chromatography eluant.

Analysis for $C_{25}H_{35}NO_8$ (MW 477.56): Calcd.: C, 62.88; H, 7.39; N, 2.93. Found: C, 62.53; H, 7.35; N, 2.91.

EXAMPLE 25

1,4-Imino-1,4-dideoxy-L-arabinitol, triisobutyrate

The title compound was prepared by the method of Example 21 by using the product of Example 24 instead of the product of Example 20.

Analysis for $C_{17}H_{29}NO_6 \cdot \frac{1}{4}H_2O$ (MW 347.92): Calcd.: C, 58.70; H, 8.55; N, 4.03. Found: C, 58.63; H, 8.53; N, 4.38.

EXAMPLE 26

1,4-(Butylimino)-1,4-dideoxy-L-arabinitol, tributyrate

The title compound was prepared by the method of Example 20 by using the product of Example 4 instead of the product of Example 17, by using butyric anhydride instead of acetic anhydride, and by using 10% ethyl acetate-hexane as the chromatography eluant.

Analysis for $C_{21}H_{37}NO_6$ (MW 399.53): Cald.: C, 63.13; H, 9.34; N, 3.51 Found: C, 63.34; H, 9.36; N, 3.47.

EXAMPLE 27

1,4-(Benzoylimino)-1,4-dideoxy-L-arabinitol, triacetate

To a solution of the title product of Example 21 (188 mg, 0.726 mmole) in 5 ml of dichloromethane was added triethylamine (146 mg, 1.45 mmoles) and then benzoyl chloride (123 mg, 0.871 mmole). After stirring overnight at room temperature, 25 ml of dichloromethane was added. The resulting solution was washed with dilute hydrochloric acid and with water. After drying over anhydrous sodium sulfate, the solution was filtered and the solvent removed on a rotary evaporator. Radial chromatography of the residue on silica gel using 75% ethyl acetate-hexane as eluant gave the title compound (222 mg) as an oil.

Analysis for $C_{18}H_{21}NO_7$ (MW 363.37): Calcd.: C, 59.49; H, 5.83; N, 3.86. Found: C, 59.26; H, 5.91; N, 3.72.

EXAMPLE 28

1,4-(Phenylacetylimino)-1,4-dideoxy-L-arabinitol, triacetate

To a solution of the title product of Example 21.(290 mg, 1.12 mmoles) in 7.5 ml of dichloromethane was added phenylacetic anhydride (341 mg, 1.34 mmoles), triethylamine (271 mg, 2.68 mmoles), and 2 mg of 4-dimethylaminopyridine. After stirring overnight at room temperature, the mixture was diluted with dichloromethane. The resulting solution was washed successively with water, aqueous sodium bicarbonate solution, dilute hydrochloric acid, and water. After drying over anhydrous sodium sulfate, the solution was filtered and the solvent removed on a rotary evaporator. Radial chromatography of the residue on silica gel using 75% ethyl acetate-hexane as eluant gave the title compound (249 mg) as a colorless oil.

Analysis for $C_{19}H_{23}NO_7$ (MW 377.40): Calcd.: C, 60.47; H, 6.14; N, 3.71. Found: C, 60.33; H, 6.21; N, 3.69.

EXAMPLE 29

1,4-(Benzyloxycarbonylimino)-1,4-dideoxy-L-arabinitol, tripropionate

The title compound was prepared by the method of Example 24 by using propionic anhydride instead of isobutyric anhydride.

Analysis for $C_{22}H_{29}NO_8$ (MW 435.48): Calcd.: C, 60.67; H, 6.71; N, 3.22. Found: C, 60.53; H, 6.70; N, 3.20.

EXAMPLE 30

1,4-Imino-1,4-dideoxy-L-arabinitol, tripropionate

The title compound was prepared by the method of Example 25 by using the product Example 29 instead of the product of Example 20.

Analysis for $C_{14}H_{23}NO_6 \cdot \frac{1}{2}H_2O$ (MW 301.34): Calcd.: C, 55.40; H, 7.72; N, 4.61. Found: C, 55.39; H, 7.90; N, 4.67.

EXAMPLE 31

1,4-(Propionylimino)-1,4-dideoxy-L-arabinitol, triacetate

The title compound was prepared as a colorless oil by the method of Example 28 by using propionic anhydride instead of phenylacetic anhydride.

Analysis for $C_{14}H_{21}NO_7$ (MW 315.33): Calcd.: C, 53.35; H, 6.71; N, 4.44. Found: C, 52.97; H, 6.79; N, 4.33.

EXAMPLE 32

1,4-(2-Methylpropionylimino)-1,4-dideoxy-L-arabinitol, triacetate

The title compound was prepared as a colorless oil by the method of Example 28 by using isobutyric anhydride instead of phenylacetic anhydride.

Analysis for $C_{15}H_{23}NO_7 \cdot \frac{1}{2}H_2O$ (MW 333.85): Calcd.: C, 53.97; H, 7.09; N, 4.20. Found: C, 54.06; H, 7.05; N, 4.22.

EXAMPLE 33

5-Benzyloxy-1-hexene

To a stirred mixture of sodium hydride (2.6g, 110 mmoles) in tetrahydrofuran (185 ml) under a nitrogen atmosphere was added a solution of 5-hexene-1-ol (10g, 100 mmoles) in tetrahydrofuran (15 ml). After stirring at room temperature for 0.5 hour, the mixture was briefly heated to reflux and then cooled. Benzyl bromide (21.4 g, 125 mmoles) was added, and the mixture was stirred at reflux for one hour. Stirring was continued overnight at room temperature, after which the mixture was concentrated on a rotary evaporator. The mixture was poured into water, and the aqueous layer was extraced with three portions of ether. The combined organic estracts were dried over sodium sulfate, filtered, and the solvent evaporated. Chromatography of the residue on silica gel using a gradient of 0 to 10% ethyl acetate-hexane as eluant gave the title product (11.2 g) as an oil. The structure was confirmed by $^1H$ NMR spectrometry.

EXAMPLE 34

5-Benzyloxy-1-pentanal

A solution of 5-benzyloxy-1-hexene prepared according to Example 33 (11.2 g, 58.9 mmoles) in dichloromethane (200 ml) at $-70°$ was ozonized until a blue color persisted. The excess ozone was purged with a stream of oxygen gas, and then dimethyl sulfide (11.0 g, 177 mmoles) was added. After stirring overnight at room temperature, the volatiles were removed on a rotary evaporator. The residue was taken up in ether, washed with water and then brine, dried over sodium sulfate, filtered, and the solvent evaporated. Chromatography of the residue on silica gel using a gradient of 10 to 50% ethyl acetate-hexane gave the title compound (3.34 g) as an oil. The structure was confirmed by $^1H$ NMR spectrometry.

EXAMPLE 35

1,4-([5-Benzyloxypentyl]imino)-1,4-dideoxy-L-arabinitol

The title compound (689 mg) was prepared as an oil by the method of Example 6 except that 5-benzyloxy-1-pentanal prepared according to Example 34 (1.44 g) was used instead of hexanal, and the treatment with trifluoroacetic acid-water followed by ion exchange chromatography was omitted. The structure was confirmed by $^1H$ NMR spectrometry.

EXAMPLE 36

1,4-([5-Benzyloxypentyl]imino)-1,4-dideoxy-L-arabinitol, triacetate

The title compound (410 mg) was prepared as an oil by the method of Example 7 except that the product of Example 35 (564 mg) was used as the starting material. The structure was confirmed by $^1H$ NMR spectrometry.

EXAMPLE 37

1,4-([5-Hydroxypentyl]imino)-1,4-dideoxy-L-arabinitol, triacetate

A solution of the title product of Example 36 (410 mg) in absolute ethanol was hydrogenated in the presence of palladium black at 60° under a pressure of 60 pounds per square inch of hydrogen for 20 hours. The catalyst was filtered off and the solvent removed on a rotary evaporator. Chromatography of the residue on silica gel using a gradient of 75 to 100% ethyl acetate-hexane as eluant gave the title compound (230 mg) as an oil.

Analysis for $C_{16}H_{27}NO_7$ (MW 345.40): Calcd.: C, 55.65; H, 7.88; N, 4.06. Found: C, 55.38; H, 7.91; N, 4.00.

EXAMPLE 38

Various compounds as prepared above were tested for inhibition of visna virus in vitro in a plaque reduction assay as follows:

METHOD

Cell and virus propagation

Sheep choroid plexus(SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at $-70°$ C.

Plaque reduction assay

SCP cells were cultured in 6-well plates to confluence. Wells were washed two times with serum free Minimal Essential Medium (MEM) to remove FBS. 0.2ml of virus was added per well in MEM supplemented with 4mM glutamine and gentamycin. After 1 hour adsorption, the virus was aspirated from each well. The appropriate concentration of each compound in 5 ml of Medium 199 (M-199) supplemented with 2% lamb serum, 4mM glutamine, 0.5% agarose and gentamycin was added to each well. Cultures were incubated at 37° C in a humidified 5% $CO_2$ incubator for 3-4 weeks. To terminate the test: cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is total lysing of the cell monolayer.

96 well plate assay

The 96 well plate assay was performed similarly to the plaque assay above with modifications. SCP cells were seeded at $1 \times 10^4$ cells per well in 0.1 ml DME medium. When confluent, the wells were washed with serum free MEM and 25 ul of virus added in M-199 supplemented with 2% lamb serum. After 1 hour, 75 uL of medium containing test compound was added to each well containing virus. After 2-3 weeks incubation the cytopathic effect of the virus was determined by staining with a vital stain. Cell viability was measured by determining stain density using a 96 well plate reader.

Control wells without virus were completed to determine the toxicity of compounds.

RESULTS

Table 1, below, sets forth the results of the assay for the compounds of Examples 3 and 5 compared to the N-butyl derivative of 1,5-dideoxy-1,5-imino-D-glucitol (N-Bu-DNJ) as a control standard.

TABLE 1

| Compound Example No. | PLAQUE REDUCTION ASSAY | | | |
|---|---|---|---|---|
| | Concentration mM | Toxicity | % Plaque Reduction | Antiviral Activity |
| N-Bu-DNJ | 1.0 | 2 | 100 | A |
| | 0.1 | 1 | 100 | A |
| | 0.01 | 0 | 13 | I |
| | 0.001 | 0 | −74 | I |
| 3 | 1.0 | 0 | 90 | A |
| | 0.1 | 0 | 72 | A |
| | 0.01 | 0 | −64 | I |
| | 0.001 | 0 | −46 | I |
| 5 | 1.0 | 0 | 83 | A |
| | 0.1 | 0 | 10 | I |
| | 0.01 | 0 | 10 | I |
| | 0.001 | 0 | 9 | I |

A = active compound; I = inactive
Toxicity graded on 0 to 4 scale; 0 = no toxicity and 4 = total cell lyses.
N-Bu-DNJ = n-butyl-deoxynojirimycin used as a control standard.

The $EC_{50}$ concentration (mM) for inhibition of visna virus for various compounds as prepared above is shown in the following Table 2:

TABLE 2

| Compound Example No. | $EC_{50}$ (mM) |
|---|---|
| 6 | 0.125 |
| 9 | 0.1 |
| 15 | 0.1 |
| 18 | 0.1 |
| 20 | 1.0 |
| 23 | 0.001 |
| 26 | 1.0 |
| 28 | 1.0 |

EXAMPLE 39

Various compounds as prepared above were tested for enzyme inhibitory activity against alpha- and beta-glucosidase enzymes as follows:

ASSAYS FOR ALPHA-GLUCOSIDASE (YEAST) AND BETA-GLUCOSIDASE (ALMONDS)

Yeast alpha-glucosidase and almond beta-glucosidase activities were measured by a modification of the method of Evans, et al., *Phytochemistry* 22, 768-770 (1983). The modifications included 1) assay of activities at pH 7.4 in HEPES (N-2-hydroxyethylpiperazine-N'-2-ethanesulfonic acid) buffer, 2) measurement in 96 well microtiter plates and 3) inclusion of 10% DMSO in control and test samples.

The release of p-nitrophenol from the substrate p-nitrophenylglycoside was measured spectrophotometrically in the presence and absence of test compound. Each assay included a known inhibitor of the enzyme as a standard. $IC_{50}$ values were determined for compounds which inhibited the enzymes more than 50% at a 1 millimolar concentration.

ALPHA-GLUCOSIDASE INHIBITION ASSAY, pH 7.4

To 100 μl 50 mM HEPES buffer, pH 7.4, in a microtiter plate, add 20 μl test compound in DMSO (DMSO alone in control), 40 μl (0.013 units) yeast alpha-glucosidase (Sigma) in HEPES buffer and pre-incubate at room temperature for 15 minutes. Add 40 μl 1.25 mM p-nitrophenyl-alpha-D-glucopyranoside (Sigma) in HEPES buffer, as substrate, and monitor absorbance change at 405 nm in a Biotek EIA Auto-reader. Absorption change was measured at 15 to 25 minutes (reaction was linear for at least 30 minutes). Each sample was tested in triplicate. $IC_{50}$ values were determined from the linear portion of the log concentration vs % inhibition curve obtained from a minimum of 3 points. Deoxynojirimycin was used as standard inhibitor.

BETA-GLUCOSIDASE INHIBITION ASSAY pH 7.4:

To 100 μl 50 mM HEPES buffer, pH 7.4, in a microtiter plate, add 20 μtest compound in DMSO (DMSO alone in control), 40 μl (0.136 units) beta-glucosidase (Sigma) in HEPES buffer and pre-incubate at room temperature for 15 minutes. Add 40 μl 1.25 mM p-nitrophenyl-beta-D-glucopyranoside in HEPES buffer, as substrate and monitor absorbance change at 405 nm in a Biotek EIA Autoreader. Absorption change was measured at 15 to 25 minutes (reaction is linear for at least 30 minutes). Each sample was tested in triplicate. $IC_{50}$ values were determined from the linear portion of the log concentration vs % inhibition curve obtained from a minimum of 3 points. Castanospermine was used as standard inhibitor.

pH 4.8:

To 100 μl 50 mM sodium citrate buffer, pH 4.8, in a microtiter plate, add 15 μl test compound in DMSO (DMSO alone in control), 20 μl (0.017 units) beta-glucosidase (Sigma) in citrate buffer and pre-incubate at room temperature for 15 minutes. Add 25 μl 2.50 mM p-nitrophenyl-beta-D-glucopyranside in citrate buffer, as substrate. Incubate at room temperature 20 minutes (reaction is linear for at least 30 minutes). Add 50 μl 0.4M NaOH. Read absorption change at 405 nm in a Biotek EIA Autoreader. Each sample was tested in triplicate. $IC_{50}$ values were determined from the linear portion of the log concentration vs % inhibition curve obtained from a minimum of 3 points. Castanospermine was used as standard inhibitor.

The inhibitory activity against alpha- and beta-glucosidase enzymes by various compounds prepared above is shown in the following table 3:

TABLE 3

| Compound Example No. | Inhibitory Activity |
|---|---|
| 6 | α-glucosidase IC$_{50}$ = 35 μM |
| 8 | α-glucosidase IC$_{50}$ = 2.2 μM β-glucosidase IC$_{50}$ = >1000 μM at pH 4.8 and 7.4 |
| 16 | α-glucosidase IC$_{50}$ = 13 μM β-glucosidase IC$_{50}$ = >1000 μM at pH 4.8 and 7.4 |
| 18 | α-glycosidase IC$_{50}$ = 46 μM β-glucosidase IC$_{50}$ = 36 μM at pH 4.8 23 μM at pH 7.4 |
| 27 | α-glucosidase 23% at 1 mM |

EXAMPLE 40

Further testing for A. inhibition of visna virus and B. enzyme inhibitory activity against alpha- and beta-glucosidase enzymes was carried out on various compounds as prepared, above, by the assay methods described in Examples 38 and 39, respectively. The results are shown in the following Tables 4 and 5:

TABLE 4

| Compound Example No. | Visna Virus Inhibition % Inhibition mM Concn. | Toxicity | Antiviral Activity |
|---|---|---|---|
| 2 | 66%/0.1 mM | 0 | A |
|   | 33%/0.01 | 0 | I |
| 4 | 77%/1.0 | 0 | A |
|   | 76%/0.1 | 0 | A |
|   | 42%/0.01 | 0 | I |
| 7 | 100%/1.0 | 4 | — |
|   | 52%/0.1 | 2 | A |
|   | 48%/0.01 | 0 | A |
| 8 | 100%/1.0 | 3 | A |
|   | 29%/0.01 | 0 | I |
| 10 | 100%/1.0 | 4 | — |
|   | 71%/0.1 | 1 | A |
|   | 21%/0.01 | 1 | I |
| 16 | 100%/1.0 | 3 | A |
|   | 100%/0.1 | 0 | A |
|   | 22%/0.01 | 0 | I |
| 20 | 58%/1.0 | 0 | A |
|   | 14%/0.1 | 0 | I |
| 22 | 61%/1.0 | 2 | A |
|   | −61%/0.1 | 1 | I |
| 26 | 100%/1.0 | 2 | A |
|   | 43%/0.1 | 0 | I |
| 28 | 90%/1.0 mM | 1 | A |
|   | 73%/0.1 | 0 | A |
|   | 56%/0.01 | 0 | A |
| 29 | 97%/0.1 | 0 | A |
|   | 87%/0.01 | 0 | A |
|   | 93%/0.001 | 0 | A |
| 31 | 64%/1.0 | 3 | A |
|   | 18%/0.1 | 1 | I |

TABLE 5

| Compound Example No. | Enzyme Inhibitory Activity % Inhibition at 1.0 mM Glucosidase | | |
|---|---|---|---|
| | α-Glucosidase | β-Glucosidase pH 4.8 | pH 7.4 |
| 2 | 178* | 14% | 45% |
| 3 | 15% | 12% | 5% |
| 4 | 227* | 20% | 26% |
| 8 | 2.2* | 19% | 26% |
| 16 | 13* | 34% | 31% |
| 17 | 482* | 4% | 4% |
| 20 | 18% | 5% | 6% |
| 22 | 30%** | 11%** | 2%** |
| 24 | 33* | 7% | 1% |
| 26 | 20%*** | 1%*** | 1%*** |
| 28 | 30% | 0% | 6% |
| 29 | 41%*** | 2%*** | 5%*** |

*IC$_{50}$ μM
**% Inhibition at 10 μM
***% Inhibition at 100 μM

The antiviral agents described herein can be used for administration to a mammalian host infected with a virus, e.g. visna virus or the human immunodeficiency virus, by conventional means, preferably in formulations with pharmeceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. N-alkyl, N-hydroxyalkyl and N-alkanoyl derivatives of 1,4-dideoxy-1,4-imino-L-arabinitol in which the alkyl group contains from 4 to 9 carbon atoms, the hydroxyalkyl group contains from 2 to 5 carbon atoms and the alkanoyl group contains from 3 to 12 carbon atoms.

2. 1,4-(Butylimino)-1,4-dideoxy-L-arabinitol.

3. 1,4-(Hexylimino)-1,4-dideoxy-L-arabinitol.

4. 1,4-(Nonylimino)-1,4-dideoxy-L-arabinitol.

5. 1,4-([2-Hydroxyethyl]imino)-1,4-dideoxy-L-arabinitol.

6. 1,4-([5Hydroxypentyl]imino)-1,4-dideoxy-L-arabinitol.

7. 1,4-(Propionylimino)-1,4-dideoxy-L-arabinitol.

8. 1,4-(2-Methylpropionylimino)-1,4-dideoxy-L-arabinitol.

9. Acylated derivatives of N-alkanoyl substituted 1,4,dideoxy-1,4-imino-L-arabinitol in which all the free hydroxyl groups are acylated with acyl group of from one to six carbon atoms and in which the N-alkanoyl substituents contain from 3 to 12 carbon atoms.

10. 1,4-(Propionylimino)-1,4-dideoxy-L-arabinitol, triacetate.

11. 1,4-(2-Methylpropionylimino)-1,4-dideoxy-L-arabinitol, triacetate.

* * * * *